United States Patent [19]

Wyness et al.

[11] 4,018,806

[45] Apr. 19, 1977

[54] PROCESS FOR RECOVERING SYMMETRICAL DIGLYCERIDES FROM GLYCERIDE MIXTURES

[75] Inventors: Glen Reid Wyness, Montgomery; Richard Worthington Lodge, Springdale, both of Ohio

[73] Assignee: The Procter & Gamble Company, Cincinnati, Ohio

[22] Filed: Oct. 6, 1975

[21] Appl. No.: 619,741

[52] U.S. Cl. .................. 260/428.5; 260/410.7; 260/426; 426/429; 426/601; 426/607
[51] Int. Cl.² .................. C11B 7/00; C07C 69/30
[58] Field of Search ........... 260/428.5, 426, 412.8, 260/410.7; 426/429, 607, 601

[56] References Cited

UNITED STATES PATENTS

| | | | |
|---|---|---|---|
| 2,626,952 | 1/1953 | Lange et al. | 260/410.7 |
| 2,682,550 | 6/1954 | Young et al. | 260/428.5 |
| 2,740,799 | 4/1956 | Young et al. | 260/410.7 |
| 3,012,890 | 12/1961 | Sutton et al. | 426/607 |

OTHER PUBLICATIONS

Journal of American Oil Chemists Society, vol. 48, No. 3, Mar., 1971, pp. 116–120—N. V. Lovegrem et al.

Primary Examiner—Winston A. Douglas
Assistant Examiner—P. E. Konopka
Attorney, Agent, or Firm—Louis G. Xiarhos

[57] ABSTRACT

A process for recovering symmetrical diglycerides from mixtures of mono-, di- and triglycerides is disclosed. The process comprises forming a solution of a glyceride mixture having from 5% to 60% triglyceride, from 15% to 70% symmetrical diglyceride, from 1% to 40% asymmetrical diglyceride and from 8% to 50% monoglyceride in a mixture of non-polar and polar organic solvents in a ratio of 2:1 to 20:1; inducing and maintaining crystallization of the symmetrical diglyceride, e.g., by cooling, while maintaining the temperature of the mixture below the saturation temperature of the symmetrical diglyceride and above the saturation temperature of the remaining components of the glyceride mixture; and recovering solid symmetrical diglyceride product. The process permits recovery of symmetrical diglyceride in a single crystallization step and in high purity.

12 Claims, No Drawings

PROCESS FOR RECOVERING SYMMETRICAL DIGLYCERIDES FROM GLYCERIDE MIXTURES

BACKGROUND OF THE INVENTION

This invention relates to a process for recovering symmetrical diglycerides of fatty acids from glyceride mixtures. More particularly, it relates to a process for recovering symmetrical diglycerides of high purity from glyceride mixtures by a simple crystallization method.

The preparation of symmetrical diglycerides of fatty acids has been described in the prior art. These diglycerides are of particular value in the preparation of cocoa butter substitutes which can be employed to advantage in the manufacture of confections and cosmetic materials. Symmetrical diglycerides of fatty acids can be formed by several techniques which, in general, include the partial esterification of free fatty acids with glycerol, the partial hydrolysis of fatty triglycerides, and the glycerolysis of fatty triglycerides. These methods, while effective to provide symmetrical diglycerides, result in the production of a mixture containing mono-, di-, and triglycerides and the relative proportions of these glycerides will depend upon relative proportions of reactants and the particular reaction conditions employed. The desirable separation of symmetrical diglycerides from such mixtures, as has been pointed out in Great Britain Pat. No. 1,325,924, is only achieved with some difficulty.

One approach to the provision of pure symmetrical diglycerides of fatty acids has involved the employment of a separation technique based upon the use of two liquid solvent phases. Thus, the U.S. patent of E.R. Lowrey (U.S. Pat. No. 3,826,720, issued July 30, 1974) describes a process whereby a glycerolysis mixture of mono-, di-, and triglycerides is subjected to a liquid-liquid extraction process to provide an aqueous-methanol phase rich in monoglyceride and a hexane phase rich in diglycerides and triglycerides. Liquid-liquid extraction methods are, however, relatively complex in operation, require considerable capital expenditure, and require high ratios of solvent to glyceride mixture. Moreover, the liquid/liquid separation process still necessitates recovery of the desired symmetrical diglyceride from the triglyceride also present in the hexane phase.

Another approach to the provision of symmetrical digylcerides has involved the recovery of the diglyceride from equilibrium mixtures having the desired diglyceride in high concentrations, e.g., in amounts to 90% or higher by weight of the glyceride mixture. In general, the higher the concentration of a given glyceride compound in a mixture of glycerides, the higher its saturation temperature. Consequently, a glyceride mixture having a high concentration of symmetrical diglyceride and only low concentrations of other glycerides, e.g., 1-monoglyceride, will permit crystallization of the desired symmetrical diglyceride from the glyceride mixture, e.g., by cooling, with recovery of product relatively free of other glycerides present in the mixture.

The provision of glyceride mixtures having a high concentration of symmetrical diglyceride and only low concentrations of other glycerides, while more readily adapted to efficient recovery of diglyceride, are not readily prepared without recourse to time-consuming procedures or methods requiring careful control of reaction conditions or parameters. The patents to Lange et al. (U.S. Pat. No. 2,626,952, issued Jan. 27, 1953) and Dutton et al. (U.S. Pat. No. 3,012,890, issued Dec. 12, 1961), for example, describe methods for recovering symmetrical diglyerides from glyceride equilibrium mixtures based upon multiple crystallizations at different temperatures. Pure diglyceride is obtained in high yield and purity by subsequent recrystallizations from solvents including mixtures of polar and non-polar solvents.

Similarly, the U.S. Pat. Nos. of Harwood (3,312,724, issued Apr. 4, 1967, and 3,634,473, issued Jan. 11, 1972) describe methods for the preparation of symmetrical fatty diglycerides. These methods involve careful control of reactant concentrations and equilibrium conditions to prepare glyceride mixtures having diglyceride in a high concentration. The separation of the diglyceride component is then accomplished by crystallization from a solvent such as a mixture of isopropyl alcohol and petroleum ether. The processes of the Harwood patents require the employment of controlled reaction and equilibrium conditions to produce diglyceride in the high concentrations permitting ready separation. Frequently, however, it will be desired to provide glyceride mixtures by glycerolysis reaction routes which permit considerable latitude in the control of reaction parameters. The recovery of symmetrical diglycerides from such mixtures which may contain the desired diglycerides in amounts only up to about 50% by weight of the mixture and may have an appreciable 1-monoglyceride content, e.g. from 8% or more, are especially difficult to separate by crystallization. Typical of such mixtures are the relatively crude products obtained by conventional glycerolysis of triglycerides, i.e., by the reaction of glycerol with fatty triglyceride. Such mixtures are described, for example, in the patent of Lowrey (U.S. Pat. No. 3,826,720, issued July 30, 1974).

It is an object of the present invention to provide a method for the recovery of symmetrical diglycerides of free fatty acids from mixtures of fatty glycerides.

Another object of the invention is the provision of a process for recovering symmetrical diglycerides of fatty acids from relatively crude glyceride mixtures.

Still another object of the present invention is the provision of a process for recovering symmetrical diglycerides of high purity from glyceride mixtures in a single crystallization step and from glyceride mixtures which can be prepared without the need for particular or carefully controlled reaction conditions.

These and other objects of the invention and the method by which they are accomplished will become apparent from consideration of the more detailed description hereinafter.

SUMMARY OF THE INVENTION

It has now been discovered that symmetrical diglycerides of fatty acids can be effectively recovered in a single-step crystallization operation from mixtures of glycerides containing mono-, di-, and triglycerides. It has been found that the desired recovery can be realized even from glyceride mixtures prepared by simple glycerolysis of fatty triglycerides. The process of the present invention comprises the steps of forming, at a temperature above the saturation temperature of symmetrical diglyceride, a solution of a glyceride material comprising from 5% to 60% fatty triglyceride, from 15% to 70% of symmetrical fatty digylceride, from 1% to 40% of asymmetrical fatty digylceride and from 8% to 50% fatty monoglyceride and a solvent material comprising a non-polar hydrocarbon solvent and an organic polar solvent in a ratio of non-polar to polar solvent of from 2:1 to 20:1; inducing and maintaining crystallization of solid symmetrical fatty diglyceride from the solution while maintaining the temperature of the mixture below the saturation temperature of the symmetrical fatty diglyceride and above the saturation temperature of the remaining components of the glyceride material; and recovering solid highly pure symmetrical fatty diglyceride.

DETAILED DESCRIPTION OF THE INVENTION

As used herein, the term symmetrical diglyceride refers to diglyceride compounds wherein the symmetry is with respect to the position of the acyl groups and not with respect to the precise nature of the acyl group. Thus, 1,3-distearin and 1-stearoyl-3-palmitoyl diglyceride are symmetrical diglycerides by reason of the positional symmetry of the stearoyl and palmitoyl acyl groups and notwithstandng the different acyl chain lengths in the case of 1-stearoyl-3-palmitoyl diglyceride. Similarly, 1,2-distearin and 1-stearoyl-2-palmitoyl diglyceride are considered herein as asymmetrical by reason of the positonal asymmetry of the acyl groups.

The separation process of the present invention has application to a wide variety of glyceride mixtures. These mixtures comprise mono-, di- and triglycerides containing fatty acyl groups which have from 12 to 22 carbon atoms. The acyl groups can be saturated or unsaturated although best results will be obtained when the acyl groups are substantially either saturated or unsaturated. The process is especially applicable to the treatment of mixtures of glycerides wherein the fatty acyl groups have from 16 to 18 carbon atoms since the diglycerides recovered therefrom, e.g., 1,3-dipalmitin, 1,3-distearin and 1-stearoyl-3-palmitoyl diglyceride, are especially useful as intermediates in the formation of cocoa-butter substitutes. The glyceride materials which comprise the starting materials of the separation process of the present invention comprise an admixture of from 5% to 60% triglyceride; from 15% to 70% symmetrical diglyceride; from 1% to 40% asymmetrical diglyceride; from 8% to 50% monoglyceride; and from 0% to 10% glycerine. These mixtures can be prepared by a number of ways as mentioned hereinbefore, and depending upon the reaction conditions employed and the relative proportions of reactants employed in their preparation, considerable variation within the amounts stated is possible.

It is especially to be noted that the glyceride materials from which the desired symmetrical diglyceride is recovered have an appreciable content, at least 8% of monoglyceride. The monoglyceride component is comprised of from 50% to 100% by weight of 1-monoglyceride. Typically, the monoglyceride will be a mixture of 1- and 2-monoglycerides, where the 1-monoglyceride content comprises at least 90%. The monoglyceride component, especially, hampers recovery of the desired symmetrical diglyceride. This is due to the close or overlapping nature of the saturation temperatures of the symmetrical diglyceride and 1-monoglyceride components. The glyceride starting materials of the present process, however, contain up to 50% monoglyceride which makes the desired separation of diglyceride especially difficult by conventional crystallization methods. The separation process of the present invention permits the recovery of diglyceride in high purity even from such mixtures.

The starting glyceride materials of the present invention are also characterized by a content of the desired diglyceride of only up to 70% and as little as 15%. Thus, these glyceride materials may be considered crude mixtures relative to the diglyceride content of mixtures prepared under more carefully controlled reaction or equilibrium conditions which assure maximum symmetrical diglyceride formation. The glyceride starting materials of the present invention while crude relative to those mixtures which might be obtained by careful control of reaction conditions are relatively simple to prepare without need for the employment of special apparatus or rigid control of reaction or equilibrium conditions.

The glyceride starting materials can contain minor amounts of non-glyceride components as is typically the case in equilibrium mixtures of mono-, di- and triglycerides. Thus, minor amounts of free fatty acid, unreacted glycerol, unsaponifiables, water and traces of inorganic salts or catalyst residues can be present in the glyceride material without affect on the conduct of the recovery process of the invention.

A particularly useful glyceride starting material is a glyceride mixture obtained by simple glycerolysis of a monoglyceride; by the reaction of from about 0.4 to 1.5 moles of glycerol per mole of the triglyceride. Typically, such a mixture will be obtained by heating the triglyceride and glycerol reactants in the presence of a catalyst such as sodium methoxide until an equilibrium state is reached. The catalyst is deactivated and a glyceride mixture results having, typically, from 10% to 35% triglyceride; from 20% to 50% symmetrical diglyceride; from 15% to 25% asymmetrical diglyceride; from 10% to 35% monoglyceride; and from 0% to 10% unreacted glycerol. The separation process of the present invention has its most advantageous application to glyceride mixtures obtained by simple glycerolysis reactions. It will be appreciated, however, that the process can be employed for the recovery of symmetrical diglyceride from mixtures having the amounts and proportions of mono-, di- and triglyceride as set forth hereinbefore, though such mixtures may be prepared by other methods. Thus, reaction mixtures which comprise monoglyceride, diglyceride, triglyceride and unreacted glycerol, as hereinbefore defined, and prepared, for example, by superglycerination of natural fats or by ester interchange of natural fats and lower-chain fatty triglycerides, such as triacetin, can likewise be employed.

The separation process of the present invention is conducted by forming a solution of the glyceride starting material and a mixture of non-polar and polar solvents and inducing the crystallization of the desired symmetrical diglyceride so as to recover the diglyceride in a single crystallization step. It has been found that the employment of both non-polar and polar solvents is essential to the recovery of the desired diglyceride in high purity and in a single step. While applicants do not wish to be bound by any precise theory as to the mechanism by which the desired separation is realized, it is believed that the polar solvent serves to suppress the crystallization or precipitation of 1-monoglyceride and other glycerides so as to permit crystallization of the diglyceride material in pure form.

The non-polar solvent is employed in predominant amount. Suitable non-polar solvents are those which permit the formation, with addition of an organic polar solvent, of a solution with the starting glyceride material. The solvent should also be substantially inert or nonreactive and should not contain any reactive constituent either as a part of the structure of the solvent or as impurity as to react with the glyceride components or otherwise interfere with desired symmetrical diglyceride separation. Suitable non-polar solvents are the hydrocarbon solvents which are normally liquid and which include aliphatic hydrocarbons, e.g., alkanes, alkenes, alkynes, cycloaliphatic hydrocarbons, aromatic hydrocarbons, or mixtures thereof.

Examples of suitable non-reactive hydrocarbon solvents include pentane, hexane, heptane, octane, 1-octene, cyclohexane, benzene, naphtha, "Stoddard" solvent, toluene and mixed xylenes. Preferred solvents are the hydrocarbons of from 5 to 10 carbon atoms which tend to be sufficiently nonvolatile as to permit ready handling but which are sufficiently volatile as to permit removal of solvent from the desired diglyceride material. Examples of preferred solvents are hexane, heptane, and benzene.

The organic polar solvent used in the practice of the present invention is a polar solvent capable of forming a solution with the glyceride starting material and the non-polar hydrocarbon solvent and which is substantially non-reactive or inert to the glyceride material or non-polar solvent. The polar solvent should be sufficiently polar as to dissolve or otherwise suppress the crystallization of 1-monoglyceride with desired diglyceride. It will be appreciated that solvents or mixtures thereof will vary in their degree of polarity and that, accordingly, amounts of polar solvents employed for this purpose will vary.

Suitable polar alcohol solvents include the alkanols of from 1 to 5 carbon atoms, e.g., methanol, ethanol, isopropanol, butanol, amyl alcohol, n-pentanol and the like. Preferred polar solvents are methanol, ethanol and isopropanol which provide good separation results and which are readily available and conveniently utilized. Moreover, their boiling points permit ready handling at room temperatures nd efficient removal from the desired diglyceride product.

Among the aliphatic, aromatic, mixed aliphatic-aromatic and cycloaliphatic ether compounds which are suitable as polar solvents are dibutyl ether, anisole, diphenyl ether, ethylphenyl ether, dioxane, 1,2-dimethoxyethane, diethylene glycol dimethyl ether tetrahydrofuran and pyran. Amine compounds which can serve as solvents include tripropyl amine, pyridine and morpholine. Still other compounds which are suitable are N,N-dialkyl amides such as dimethyl formamide and dimethyl acetamide; dialkyl sulfoxides such as dimethyl sulfoxide; nitriles such as acetonitrile, propionitrile, butyronitrile and valeronitrile; ketones such as acetone and dimethyl ketone; and low molecular weight alkyl esters of alkanoic acids, such as ethyl acetate, amyl acetate, propyl acetate and ethyl propionate. The polar materials set forth herein are exemplary of polar organic solvents useful herein and are not intended as being limiting. It will be appreciated that any polar solvent or mixture of polar solvents which is capable of dissolving the glyceride mixture and the 1-monoglyceride content thereof and which is compatible with the glyceride starting material and the hydrocarbon non-polar solvent can be suitably employed.

The non-polar and polar solvents are utilized in a ratio of non-polar to polar solvent by weight of from 2:1 to 20:1. The ratio of solvents employed will depend upon the nature of the glyceride starting material, the relative amounts of the glyceride components in the mixture, and the relative polarity of polar solvent. In general, a ratio of from 2:1 will be employed for those mixtures having the greatest amount of 1-monoglyceride so as to assure a sufficient amount of polar solvent to promote the solubility of the monoglyceride content of the glyceride mixture. Similarly, higher ratios of non-polar to polar solvent will be employed where the amount of monoglyceride is at its lowest. Normally, a ratio of non-polar to polar solvent higher than about 20:1 will not be utilized as the contribution of the polar solvent will tend to be minimized. A preferred ratio is from 3:1 to 15:1 and provides best results for the glyceride mixtures normally resulting from glycerolysis reactions.

The amount of non-polar and polar solvent utilized herein will depend upon the amount of the glyceride starting material to be treated, the relative amounts of the components of the glyceride material, and solvent polarity. Normally, a mixture of the non-polar and polar solvents will be prepared and the mixture will be utilized to form a solution with the fatty glyceride starting material. It has been found essential to the recovery of high purity symmetrical diglyceride that a homogeneous mixture be prepared. The solvent mixture employed, like the ratio of non-polar to polar solvent, should be sufficient to assure the solubility of the glyceride mixture including its monoglyceride content. Accordingly, the amount of solvent mixture will vary with the nature of the glyceride starting material and with the polarity of the solvent mixture.

Amounts of solvent mixture in excess of about 95% by weight of the glyceride mixture and solvents will not normally be employed for reasons of economy and convenience. When the diglyceride is to be crystallized from solution by evaporation of solvent, it will be appreciated that excessive amounts of solvent will be desirably avoided for reasons of economy of operation. Best results are achieved when a solvent mixture in a ratio of non-polar to polar solvent of from 3:1 to 15:1 is employed in an amount such that the solvent comprises by weight from about 35% to about 95% by weight of the glyceride and solvent mixture.

The solution of glyceride starting material and solvents is treated so as to induce crystallization of the desired symmetrical digylceride component. Crystallization can be induced in several ways. This can be conveniently accomplished by cooling the solution so that the solubility of the desired symmetrical diglyceride will be diminished sufficiently as to cause the formation of crystals of symmetrical diglyceride. The saturation temperature of a glyceride component, as used herein, refers to the temperature at which the glyceride is present in an amount in excess of solubility and at which it can solidify or crystallize. Since the saturation temperature in the solution of symmetrical diglyceride is above the temperature at which the remaining components of the glyceride starting material solidfy or crystallize, the symmetrical diglyceride can be effectively separated from the solution in high purity.

While the desired crystallization or solidification of symmetrical diglyceride may commence at the saturation temperature, frequently the solution will undergo supercooling and appreciable crystallization of diglyceride will occur at a somewhat lower temperature. Temperatures lower than the saturation temperature can be employed and will increase crystal size and yield. It will be appreciated, however, that the temperature should not be reduced sufficiently as to coincide with or go below the saturation temperature of other components of the glyceride mixture in the solution and thereby cause contamination of the desired symmetrical diglyceride material. Good results are frequently and conveniently obtained by conducting the crystallization at a temperature of about 1° (Fahrenheit) below the clouding temperature, which is the temperature at which the solution is observed to become clouded in appearance.

Other techniques for recovering symmetrical diglyceride from the solution can be employed. For example, solvent removal can be utilized. This technique can be applied in conventional fashion to cause the symmetrical diglyceride to be present in excess of its solubility and thereby be recovered from the glyceride mixture. Symmetrical diglyceride from an independent source can also be employed to promote crystallization by the known technique of seeding. Accordingly, seeding can be employed in conjunction with cooling or solvent removal methods with good results.

The symmetrical diglyceride, upon crystallization from a solution of the glyceride mixture, can be recovered conveniently, for example, by filtration. The mixture of symmetrical diglyceride crystals and solution of remaining components can be filtered through paper so as to permit recovery of the pure symmetrical diglyceride. Washing of the recovered crystals by addition of solvent, e.g., hexane to the filter cake can be employed and best results will be obtained if the filter cake is not allowed to dry prior to addition of the washing solvent. Purity is enhanced by avoiding a cooling effect upon the drying filter cake and accompanying crystallization of undesired components.

The process of the present invention permits the recovery of symmetrical diglyceride in high purity, which as used herein, refers to purity of at least 95%. It will be appreciated that purity of the symmetrical diglyceride will be an important consideration in those instances wherein the material is to be employed in comestibles or where the material is to be used in the preparation of synthetic triglyceride fat. For example, the symmetrical diglyceride prepared by the process of the invention can be reacted with by acylating agent, e.g. oleyl chloride or anhydride, in the presence of a position-specific catalyst to provide a cocoa butter substitute which is primarily 1-stearoyl-2-oleyl-3-palmitoyl triglyceride. The purity of the triglyceride will depend in part upon the purity of the symmetrical diglyceride from which it is synethesized and, accordingly, a method which permits recovery of pure symmetrical diglycerides will be useful in the preparation of such synthetic triglyceride fats. Examples of methods for preparing triglyceride fat from symmetrical diglycerides are found in U.S. Pat. No. 3,410,881 to J. B. Martin et al. (issued Nov. 12, 1968); U.S. Pat. No. 3,808,245 to D. E. O'Connor et al. (issued April 30, 1974); U.S. Pat. Nos. 3,809,711 and 3,809,712 to J. J. Yetter (issued May 7, 1974); and U.S. Pat. No. 3,882,155 to H. W. Wharton (issued May 6, 1975).

The process of the present invention has a particular advantage insofar as it permits recovery of pure symmetrical diglyceride in a single crystallization. Thus, multiple crystallizations and recrystallizations are not required to achieve high purity. The recovery can be performed in either a batch or continuous operation.

The process of the present invention is especially useful in the separation of symmetrical diglycerides from relatively crude glyceride mixtures and will, therefore, lend itself to the treatment of mixtures which ordinarily might not be attractive by reason of the relative impurity of the mixture. Thus, advantage may be taken of the relative simplicity and ease of operation of simple triglyceride glycerolysis reactions and the reaction product can be simply and effectively treated to provide the symmetrical diglyceride component in high purity.

The following examples are illustrative of the process of the invention. The examples are not intended to limit the scope of the invention set forth in the appended claims. In each example, washing was performed by passing hexane, at the temperature of crystallization, through the recovered symmetrical diglyceride product. Unless otherwise specified, all percentages in the following examples are by weight.

EXAMPLE I

A. Glycerolysis of Hydrogenated Palm Oil

Into a flask were added 146 grams of glycerol and 11.26 grams of a 50% aqueous solution of sodium hydroxide. The mixture was heated to 300° F for ½ hour and was subjected to a vacuum to remove water from the mixture. The resulting solution was added with agitation to 2000 grams (molar ratio of palm oil to glycerol, 1.48) of fully hydrogenated palm oil (IV less than 4) which had been melted by heating to 200° F. The resulting two-phase mixture was heated to 300° F and maintained at 300° F for 1 hour so as to complete the reaction and allow for equilibration of the reaction mixture which was comprised of a single phase. The catalyst was deactivated by addition of 11.5 grams of 75% phosphoric acid to the reaction product and the product was dried under vacuum. Sodium salts formed by addition of phosphoric acid were removed by filtration under vacuum through a Buchner funnel. The reaction mixture, excluding unreacted glycerol, was shown by thin layer chromatographic analysis to contain 35% triglyceride; 31% 1,3-diglyceride; 15% 1,2-diglyceride; 2% 2-monoglyceride; 15% 1-monoglyceride; and 2% free fatty acid. Analysis for unreacted glycerol showed the glycerol to be present in the mixture in an amount of 1%.

B. Separation of 1,3-Diglyceride

Into a 250 ml. Erlenmeyer flask were added 66 grams of the mixed glyceride product prepared in Part A of EXAMPLE I, 15 grams methanol and 69 grams hexane. The resulting mixture was heated to effect complete dissolution. The solution was then cooled with agitation by a cooling plate adapted with circulating water and cooling means for the circulating water. The solution was cooled until clouding was observed, which corresponded to a temperature of 88° F. The saturation temperature for the 1,3-diglyceride in the mixture was determined by heating the mixture slowly until all of the crystals were observed to dissolve, which corresponded to a temperature of 98° F. The mixture was then cooled again to 87° F and held at that temperature for one hour with the result that crystallization was induced and precipitation of crystals observed. The resulting crystals were separated by filtration under vacuum through a Buchner funnel. The resulting crystals were washed by passing 87° F hexane through the crystalline product. The dry crystalline product, in an amount of 8.44 grams, was found upon thin layer chromatographic analysis to consist of 1,3-diglyceride product and only a trace of triglyceride, i.e., to have a purity in excess of 99% 1,3-diglyceride.

EXAMPLE II

The process and procedures of EXAMPLE I were repeated except that 24 grams of the glyceride product of Part A were added to 9 grams of methanol and 117 grams of hexane. The clouding temperature was 77° F while the saturation temperature was 84° F. The crystallization was conducted at 73° F and 3.29 grams of crystalline product were recovered. Thin layer chromatographic analysis showed the product to consist of 1,3-diglyceride in excess of 99% and a trace of triglyceride.

EXAMPLE III

A. Glycerolysis of Hydrogenated Palm Oil

Glycerolysis of completely hydrogenated palm oil was conducted utilizing the procedure of Part A of EXAMPLE I, except that 2000 grams of the palm oil, 270 grams of glycerine, 11.3 grams of 50% aqueous sodium hydroxide and 11.9 grams of 75% aqueous phosphoric acid were employed. The molar ratio of palm oil to glycerol was 0.8. The reaction mixture, excluding unreacted glycerol, was shown by thin layer chromatographic analyis to contain 22% triglyceride; 30% 1,3-diglyceride; 20% 1,2-diglyceride; 1% free fatty acid; 2% 2-monoglyceride; and 25% 1-monoglyceride. Analysis for unreacted glycerol showed the glycerol to be present in the mixture in an amount of 2.4%.

B. Separation of 1,3-diglyceride

The crystallization procedure of Part B of EXAMPLE I was employed except that 51 grams of the product of Part A of EXAMPLE III, 15 grams of methanol and 84 grams of hexane were employed. The clouding point corresponded to 88° F while the saturation temperature was 94° F. The crystallization was conducted at 87.5° F and 2.7 grams of crystalline product were recovered. Thin layer chromatographic analysis showed the product to consist of 99% 1,3-diglyceride and 1% 1-monoglyceride.

EXAMPLE IV

A. Glycerolysis of Hydrogenated Palm Oil

Glycerolysis of completely hydrogenated palm oil was conducted utilizing the procedure of Part A of EXAMPLE I, except that 2000 grams of the palm oil, 181 grams of glycerine, 11.3 grams of 50% aqueous sodium hydroxide and 11.9 grams of 75% aqueous phosphoric acid were employed. The molar ratio of palm oil to glycerol was 1.2. The reaction mixture, excluding unreacted glycerol, was shown by thin layer chromatographic analysis to contain 25% triglyceride; 38% 1,3-diglyceride; 20% 1,2-diglyceride; 1% free fatty acid; 1% 2-monoglyceride; and 15% 1-monoglyceride. Analysis for unreacted glycerol showed the glycerol to be present in the amount of 0.83%.

B. Separation of 1,3-Diglyceride

The crystallization procedure of Part B of EXAMPLE I was employed except that 45 grams of the product of Part A of EXAMPLE IV, 13.13 grams of methanol and 91.88 grams of hexane were employed. The clouding point corresponded to 84° F while the saturation temperature was 91° F. The crystallization was conducted at 80° F and 6.2 grams of crystalline product were recovered. Thin layer chromatographic analysis showed the product to consist of 99% 1,3-diglyeride and 1% 1-monoglyceride.

EXAMPLE V

A. Glycerolysis of Hydrogenated Palm Oil

Fully hydrogenated palm oil (Iodine value less than 4) was fed into a reaction vessel in an amount of 8000 pounds and was agitated by steam sparging. The oil was heated to 250° F and 770 pounds of glycerol (corresponding to a mole ratio of triglyceride to glycerol of 1.13) and 97 pounds of a 47% aqueous sodium hydoxide solution were added. The reaction mixture was dried for 15 minutes by application of a vacuum (1 psia at 260° F). The reaction mixture was brought to 300° F and allowed to react for one hour. Forty-eight pounds of an aqueous 75% phophoric acid solution were added to inactivate the alkaline catalyst, vacuum was then applied for one hour in order to remove the glycerine, and the reaction mixture was then cooled. Sodium salts were removed by filtration and a glyceride reaction mixture was obtained. The reaction mixture, excluding unreacted glycerol, was shown by thin layer chromatographic analysis to contain 25% triglyceride; 35%, 1,3-diglyceride, 20% 1,2-diglyceride, 3% free fatty acid, 2% 2-monoglyceride, and 15% 1-monoglyceride. Analysis for unreacted glycerol showed the glycerol to be present in the mixture in an amount less than 0.1%.

Separation of 1,3-Diglyceride

The crystallization procedure of Part B of EXAMPLE I was employed except that 30 grams of the product of Part A of EXAMPLE V, 18 grams of ethanol and 102 grams of hexane were employed. The clouding point corresponded to 82.5° F, while the saturated temperature was 89° F. The crystallization was conducted at 81° F and 4 grams of crystalline product were recovered. Thin layer chromatographic analysis showed the product to consist of 99% 1,3-diglyceride and 1% triglyceride.

EXAMPLE VI

The following experiments were conducted to determine the results of attempted crystallizations utilizing a single solvent material or a mixture of non-polar and polar solvents. In one experiment, 20 grams of the glyceride mixture product of Part A of EXAMPLE V was added with stirring to 280 grams of hexane (no polar solvent) with the result that a solution was obtained. The solution was cooled with agitation on a cooling plate and crystallization was allowed to take place at 92° F (1° below the cloud point temperature). Very few crystals were precipitated (less than 1 gram). The resulting crystalline product was filtered and analyzed by thin layer chromatography with the result that the product was shown to contain 98% 1-monoglyceride.

In another experiment, 20 grams of the same mixed glyceride (from Part A, EXAMPLE V) was added to 280 grams of isopropanol (no non-polar solvent) with the formation of a solution. The solution was cooled and crytallization was allowed to take place at 95° F (1° lower than the cloud point temperature). A crystalline product was filtered and analyzed by thin layer chromatography. The product consisted of 89% triglyceride, 6% 1,3-diglyceride, 3% 1,2-diglyceride and 2% 1-monoglyceride.

In still another experiment, 20 grams of the same mixed glyceride (from Part A, EXAMPLE V) was added to 42 grams of iopropanol and 238 grams of hexane. The resulting homogenous solution was cooled and crystallization was allowed to take place at 62° F (1° lower than the cloud point temperature). A crystalline product (2.5 grams) was filtered and analyzed by thin layer chromatography. The product consisted of 1,3-diglyceride in an amount in excess of 99% purity and a trace of triglyceride.

What is claimed is:

1. A process for recovering 1,3-digylceride from a glyceride mixture comprising from 5% to 60% triglyceride, from 15% to 70% 1,3-diglyceride, from 1% to 40% 1,2-diglyceride and from 8% to 50% monoglyceride which comprises: forming a solution of a glyceride mixture comprising from 5% to 60% triglyceride, from 15% to 70% 1,3-diglyceride, from 1% to 40% 1,2-diglyceride and from 8% to 50% monoglyceride, the acyl groups of said glycerides having from 12 to 22 carbon atoms and a non-polar hydrocarbon solvent and polar organic solvent, in a ratio of non-polar hydrocarbon solvent to polar organic solvent of from 2:1 to 20:1, said polar organic solvent being sufficiently polar as to dissolve the monoglyceride content of said glyceride mixture; inducing and maintaining crystallization of solid 1,3-diglyceride from the solution while maintaining the temperature of the solution below the saturation temperature of the 1,3-diglyceride and above the saturation temperature of the remaining components of the glyceride mixture; and recovering solid highly pure 1,3-diglyceride.

2. The process of claim 1 wherein the crystallization of 1,3-diglyceride is induced by cooling the solution of glyceride mixture and non-polar hydrocarbon and polar organic solvents from a temperature above the saturation temperature of said 1,3-diglyceride saturation temperature to a temperature below the saturation temperature of said 1,3-diglyceride saturation temperature.

3. The process of claim 1 wherein the crystallization of 1,3-diglyceride is induced by removing solvent.

4. The process of claim 1 wherein the ratio of non-polar hydrocarbon solvent to polar organic solvent is from 3:1 to 15:1.

5. The process of claim 1 wherein the glyceride mixture comprises from 10% to 35% triglyceride, from 20% to 50% 1,3-diglyceride, from 15% to 25% 1,2-diglyceride, from 10% to 35% monoglyceride and from 0% to 10% glycerol.

6. The process of claim 1 wherein the glyceride mixture is a mixture of glycerides obtained by reaction of a fatty triglyceride wherein the fatty moieties are substantially saturated and have from 12 to 22 carbon atoms with glycerol in a molar ratio of glycerol to fatty triglyceride of from 0.4:1 to 1.5:1.

7. The process of claim 1 wherein the polar organic solvent is a lower alkanol having from 1 to 5 carbon atoms.

8. The process of claim 1 wherein the solution of the glyceride mixture and non-polar hydrocarbon and polar organic solvents is formed by mixing the glyceride mixture and solvents in amounts such that the solvents comprise from 35% to 95% by weight of the combined weight of said glyceride mixture and solvents.

9. The process of claim 7 wherein the crystallization of 1,3-diglyceride is induced by cooling from a temperature above the saturation temperature of said 1,3-diglyceride to a temperature below the saturation temperature of said 1,3-diglyceride.

10. The process of claim 5 wherein the non-polar hydrocarbon solvent has from 5 to 10 carbon atoms and the polar organic solvent is a lower alkanol having from 1 to 5 carbon atoms.

11. The process of claim 10 wherein the solvents comprise from 35% to 95% by weight of the combined weight of the glyceride mixture and solvents and wherein the ratio of the hydrocarbon solvent to lower alkanol is from 3:1 to 15:1.

12. The process of claim 11 wherein the crystallization of 1,3-diglyceride is induced by cooling the solution of glyceride mixture and hydrocarbon and alkanol solvents from a temperature above the saturation temperature of said 1,3-diglyceride saturation temperature to a temperature below the saturation temperature of said 1,3-diglyceride saturation temperature.

* * * * *

UNITED STATES PATENT AND TRADEMARK OFFICE
CERTIFICATE OF CORRECTION

PATENT NO. : 4,018,806
DATED : April 19, 1977
INVENTOR(S) : Glen R. Wyness and Richard W. Lodge It is certified that error appears in the above-identified patent and that said Letters Patent are hereby corrected as shown below:

| Col. | Line | |
|---|---|---|
| 3 | 15 & 16 | "digylceride" should be -- diglyceride -- |
| 3 | 42 | "positonal" should be -- positional -- |
| 4 | 42 | "monoglyceride" should be -- triglyceride -- |
| 4 | 42 | delete the semicolon |
| 5 | 56 | "nd" should be -- and -- |
| 7 | 6 | "solidfy" should be -- solidify -- |
| 7 | 60 | "by" should be -- an -- |
| 9 | 30 | insert -- purity -- after "99%" |
| 9 | 43 | "analyis" should be -- analysis -- |
| 10 | 35 | "phophoric" should be -- phosphoric -- |
| 11 | 12 | "crytallization" should be -- crystallization -- |

Signed and Sealed this second Day of August 1977

[SEAL]

Attest:

RUTH C. MASON
Attesting Officer

C. MARSHALL DANN
Commissioner of Patents and Trademarks